United States Patent [19]

Latenser et al.

[11] 4,142,529

[45] Mar. 6, 1979

[54] PROCESS AND DEVICE FOR THE THERAPEUTIC TREATMENT OF HEMORRHOIDS

[75] Inventors: James S. Latenser; Roger Q. Estes; Gerald I. Connor, all of Spokane, Wash.

[73] Assignee: Bio-Tronics, Inc., Spokane, Wash.

[21] Appl. No.: 807,827

[22] Filed: Jun. 20, 1977

[51] Int. Cl.² .............................................. A61F 7/12
[52] U.S. Cl. .................. 128/401; 128/303.12
[58] Field of Search ...................... 128/401, 399, 303.1, 128/303.12, 254, 255, 407, 303.18, 422, 408, 172.1

[56] References Cited

U.S. PATENT DOCUMENTS

| | | | |
|---|---|---|---|
| 1,272,469 | 7/1918 | Lidberg | 128/303.12 |
| 1,280,052 | 9/1918 | Lidberg | 128/303.12 |
| 1,615,828 | 2/1927 | Chesney | 128/401 |
| 1,964,732 | 7/1934 | Homan | 128/303.12 |
| 2,074,634 | 3/1937 | Ackerman | 128/401 |
| 2,095,678 | 10/1937 | Slutz et al. | 128/401 |
| 3,170,465 | 2/1965 | Henney et al. | 128/401 |
| 3,698,394 | 10/1972 | Piper et al. | 128/303.1 |
| 3,789,853 | 2/1974 | Reinhard | 128/399 |
| 3,840,016 | 10/1974 | Lindemann | 128/408 |
| 3,901,224 | 8/1975 | Bucalo | 128/401 X |
| 3,902,502 | 9/1975 | Liss et al. | 128/422 |
| 3,911,924 | 10/1975 | Zimmer | 128/303.1 |
| 3,938,526 | 2/1976 | Anderson et al. | 128/303.1 |

FOREIGN PATENT DOCUMENTS

| | | | |
|---|---|---|---|
| 109175 | 7/1939 | Australia | 128/407 |
| 1304740 | 8/1962 | France | 128/401 |

*Primary Examiner*—Lee S. Cohen
*Attorney, Agent, or Firm*—Wells, St. John & Roberts

[57] ABSTRACT

A process and device is described for therapeutically treating hemorrhoids extending from the anal canal wall of a patient. The device includes a stable, anal canal suppository appliance for intimately contacting the anal canal wall and hemorrhoids. The appliance has sufficient length to extend from the anus to the rectum and sufficient diameter to intimately contact the wall tissues without overly stretching the sphincter muscles. The appliance contains an internal electrical resistor for generating heat in response to the application of electrical energy. The device has a portable case containing an electrical energy storage battery and a control circuit for controlling the application of the electrical energy to the resistor to maintain the temperature of the appliance above body temperature and below 45° C.

9 Claims, 10 Drawing Figures

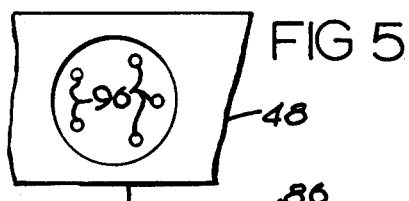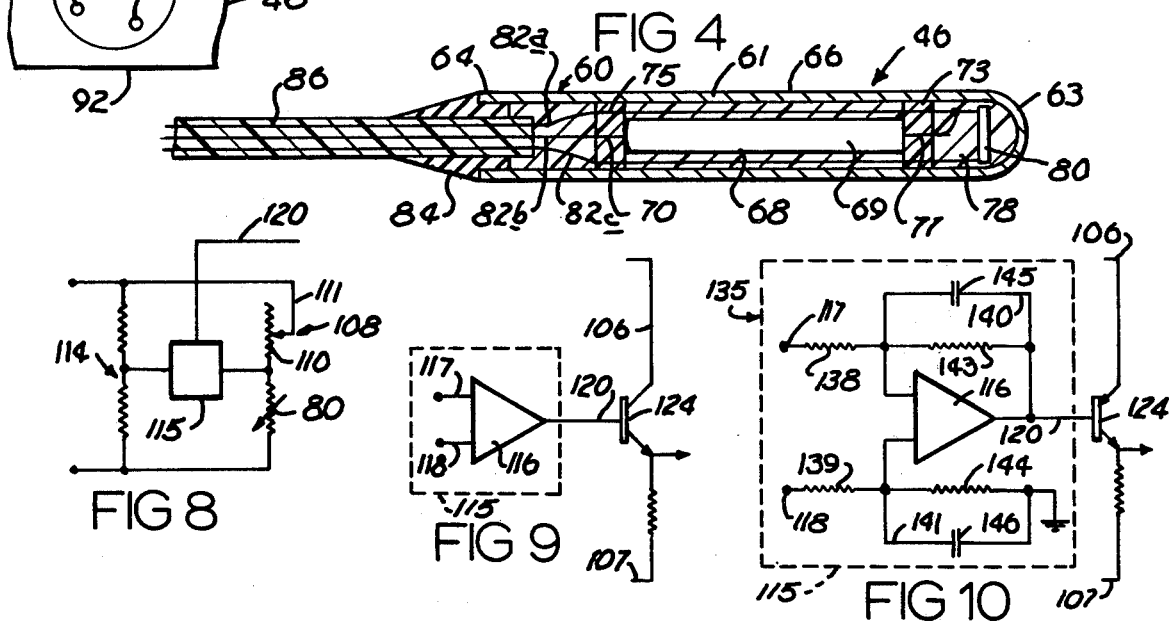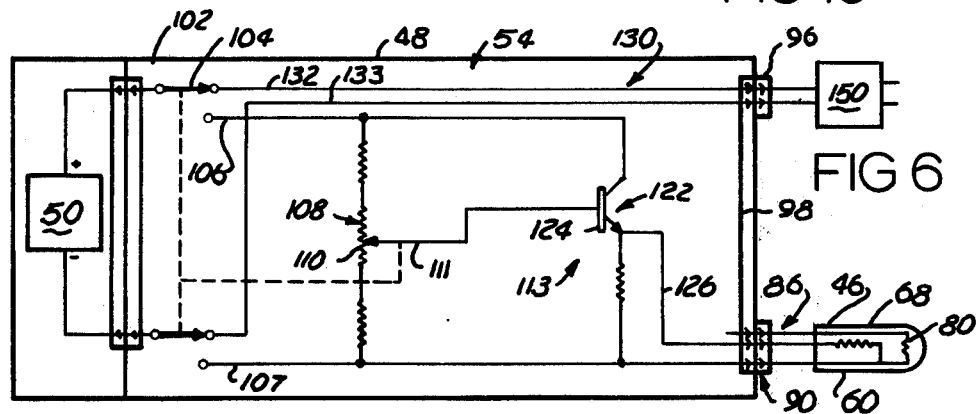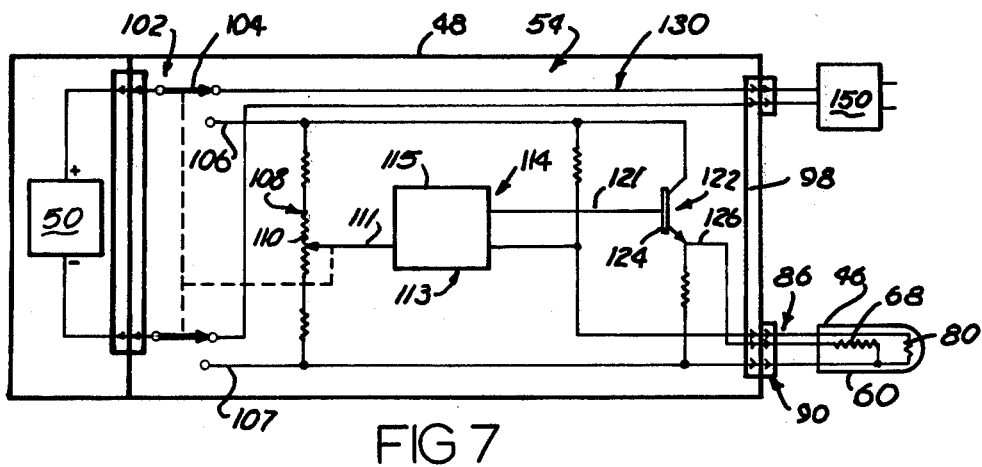

PROCESS AND DEVICE FOR THE THERAPEUTIC TREATMENT OF HEMORRHOIDS

BACKGROUND OF THE INVENTION

This invention relates to processes and devices for the therapeutic treatment of hemorrhoids. It has been estimated that approximately one third of the adults in the United States shall at one time or another have a hemorrhoidal condition that is discomforting and quite painful. It appears that hemorrhoids are more numerous in high stress societies.

Anatomically, hemorrhoids are caused by the swelling and thrombosis of a large plexus of veins in the anal canal followed by edema. Frequently hemorrhoids are considered primarily as varicose veins and their associated affects and disruptions in the anal-rectal canal. In the formation of hemorrhoids, the veins become varicose and the valves of the veins become incompetent through mechanical or vascular hydraulic stresses in excess of the elastic limits of the veinal structure. Causes of hemorrhoids are generally attributed to chronic constipation, irregularity of bowel evacuation, poor dietary habits and pregnancy-induced interference with the venous return flow due to fetal pressures against the pelvic area.

Occasionally hemorrhoids may be accompanied by fissures or cracks in the anal cavity, the base of which becomes secondarily infected causing bleeding and substantial pain.

Hemorrhoids are generally diagnosed by symptons or by their appearance in a rectal examination. The formation of hemorrhoids generally involves swelling about the anus which may become more pronounced on bowel evacuation. With a chronic case of hemorrhoids, bowel evacuation becomes extremely painful and frequently results in rectal bleeding.

Unless the hemorrhoids have reached an acute stage, treatment is generally accompanied with attention to one's diet, bowel habits and less stressful activity. Frequently a treating physician will recommend that the patient be administered sitz baths three or four times a day in water as hot as a patient can comfortably tolerate. Frequently hydrophilic, bulk stool formers such as "Metamucil" are prescribed to assist in the bowel evacuation process. Acute hemorrhoids frequently require rubber band legations and some forms of surgery.

One of the principal objects of this invention is to provide a proctologic process and device for the therapeutic treatment of hemorrhoids to reduce the hemorrhoidal swelling and discomfort.

An additional object of this invention is to provide a proctologic process and apparatus for treating hemorrhoids that provides the patient with additional techniques and devices to hopefully alleviate the hemorrhoidal condition short of surgery.

A further object and advantage of this invention is to provide a proctologic process and device for therapeutic treatment of hemorrhoids that can be administered by the patient at a time and location convenient to the patient.

A still further object of this invention is to provide a portable proctologic device that may be carried with the patient to apply the therapeutic treatment at the convenience of the patient.

These and other objects and advantages of this invention will become apparent upon reading the following detailed description of a preferred and alternate embodiment.

BRIEF DESCRIPTION OF THE DRAWINGS

A preferred and alternate embodiment of this invention is illustrated in the accompanying drawings, in which:

FIG. 4 is a longitudinal cross-sectional view of the stable anal canal suppository appliance illustrated in FIG. 3;

FIG. 5 is a fragmentary face view of a portion of the proctologic device;

FIG. 6 is an electrical schematic view of an embodiment of the proctologic device; an FIG. 7 is an electrical schematic view of an alternate embodiment of the proctologic device.

FIG. 8 is an electrical schematic of an alternate form of a bridge circuit for the proctologic device;

FIG. 9 is an electrical schematic of operational input-/output components for the proctologic device; and FIG. 10 is an electrical schematic of a continuous proportional temperature control subcircuit for the proctologic device.

DETAILED DESCRIPTION OF TWO EMBODIMENTS

Figure 1:
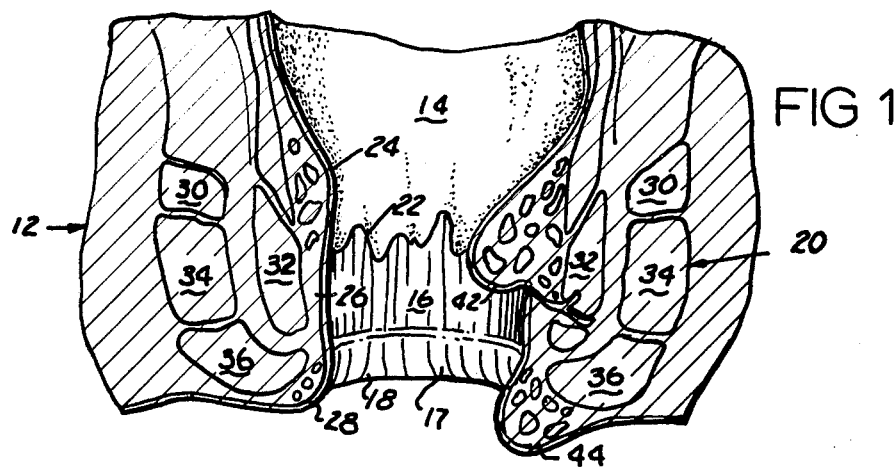
FIG. 1 is a diagrammatical cross-sectional longitudinal view of a rectal region of a human illustrating an anal canal in a dilated condition with one side of the canal illustrated having a normal anatomy with the other side of the canal illustrated with both internal and external hemorrhoids.
Figure 2:
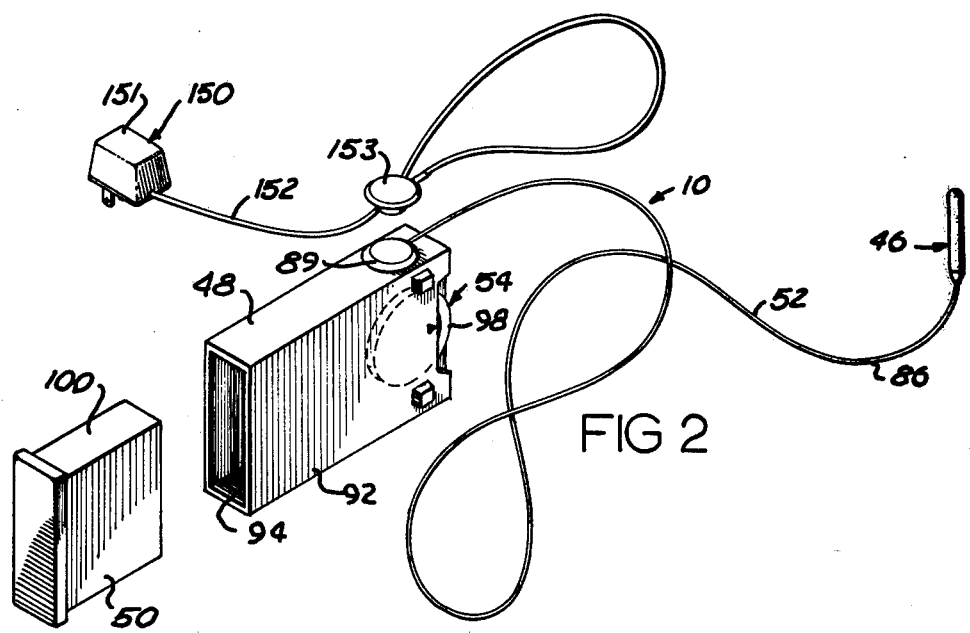
FIG. 2 is an isometric exploded view of a proctologic device for therapeutic treatment of hemorrhoids.
Figure 3:
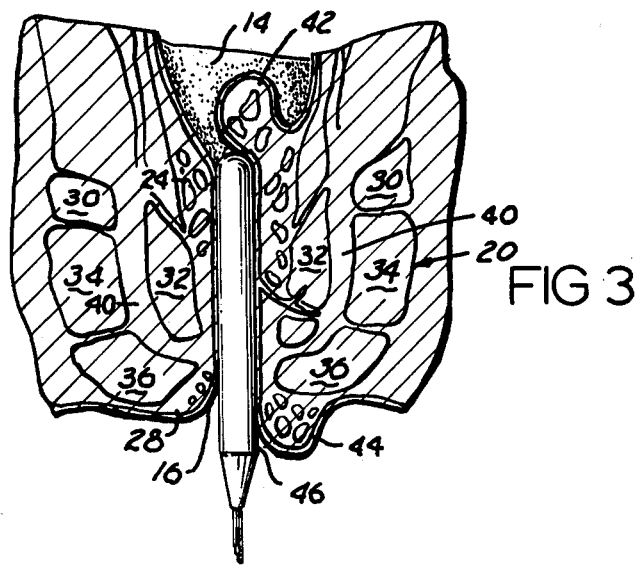
FIG. 3 is a diagrammatical cross-sectional view of the rectal region illustrated in FIG. 1 except showing the anal canal in a nondilated condition with an element of the proctologic device — namely a stable anal canal suppository appliance inserted therein.

Referring now in detail to the drawings, there is illustrated in FIG. 2 a proctologic device 10 for the therapeutic treatment of hemorrhoids which are illustrated in FIGS. 1 and 3. FIGS. 1 and 3 show, in diagrammatical cross-section, a portion of the rectal region 12 of a human being. FIG. 1 shows the rectal region 12 dilated without application of the proctologic device 10 and FIG. 3 shows an undilated rectal region 12 with an element of the device 10 inserted therein.

To understand this invention, it is desirable to be acquainted with the anatomical structure of the human rectal region 12. The rectal region 12 illustrated shows a lower portion of a rectum 14 with an anal canal 16 extending from the rectum 14 to an anus 18 that is recessed within an intergluteal cleft between the buttocks. The anal canal 16 has a mucoid surface wall 17 extending from the rectum 14 to the anus 18. The canal wall 17 transforms from a mucous membrane at the rectum 14 to an epidermal surface at the anus 18. The wall 17 is surrounded by the sphincter muscles 20.

More specifically the rectum 14 includes a rectal sinus tissue 22 at the junction between the rectum and the anal canal 16. The anal canal 16 includes an internal hemorrhoidal plexus region 24, a musculus subsucosae ani region 26 and an external hemorrhoidal plexus region 28. The sphincter muscles are subdivided into a deep external sphincter muscle 30 and an internal sphincter muscle 32, a superficial external sphincter muscle 34 and a subcutaneous external sphincter muscle tissue 36. A conjointed longitudinal muscle 40 extends longitudinally of the anal canal 16 intermediate the sphincter muscle tissues. Internal hemorrhoids 42 (FIG. 1) are formed at the internal hemorrhoidal plexus region 24 by thrombosis of the vein structure followed by edema. Likewise, when the vein structure of the external hemorrhoidal plexus region 28 becomes varicosed or abnormally dilated (thrombosis) then an external hemorrhoid 44 is formed. The presence of internal and external hemorrhoids 42 and 44 generally cause pain, itching and rectal bleeding particularly during bowel evacuation. The proctologic device 10 is provided to therapeutically treat the hemorrhoids to at least provide temporary relief from such discomfort.

The proctologic device 10 includes a stable, anal canal, suppository appliance 46 for positioning within the anal canal 16 as illustrated in FIG. 3. The proctologic device 10 includes a portable control case 48 that may be carried or held by the patient himself during the therapeutic treatment process. The portable case 48 contains an electrical storage battery 50 for generating electrical energy. A cable means 52 is connected to the appliance 46 at one end with the other end connectable to the control case 48 for transmitting electrical energy from the storage battery 50 to the suppository appliance 46 to generate internal heating of the suppository appliance 46 for direct physical contact therapeutic treatment of the canal 16.

The device 10 further includes a control means 54 incorporated in the control case 48 for controlling the application of electrical energy from the storage battery 50 through the cable means 52 to the suppository appliance 46. The control means 54 enables the patient to control the amount of electrical energy applied to the suppository appliance 46 to heat the suppository appliance 46 above the body temperature but less than 45° C. to thereby relax the sphincter muscles 20 and to facilitate the opening of the vascular channels of the hemorrhoids 42 and 44 to relieve the discomfort and to hopefully facilitate shrinkage of the hemorrhoids.

The suppository appliance 46 (FIG. 4) includes a cylindrical shell or jacket 60 having a cylindrical body portion 61 that extends from a rear end 64 to a front end or distal tip 63. The distal tip 63 is in the form of a hemisphere enclosing the front end of the jacket 60. Preferably the jacket is constructed of stainless steel; however, other materials such as teflon and polyethylene may be utilized. The jacket 60 has an exterior heat transfer surface 66 for intimately contacting the tissues of the anal canal 16. To obtain and maintain intimate contact with the anal canal tissues, including the hemorrhoids 42 and 44, it is preferable that the jacket 60 have a length between 30 millimeters and 50 millimeters to extend totally from the anus 18 through the anal canal 16 to the rectum 14. Preferably the jacket 60 has a diameter of between five millimeters and ten millimeters inclusive. Additionally, it is preferable that the heat transfer surface 66 have an area of between five square centimeters and twenty square centimeters in intimate contact with the anal canal.

The suppository appliance 46 includes an electrical resistor 68 preferably of a cylindrical type that is concentrically mounted within the jacket 60 for generating internal heat within the jacket. Preferably the resistor 68 should have an ohm rating of between 1 and 100 ohms and a power rating at less than 2 watts. The cylindrical resistor 68 preferably has a cylindrical body 69 with electrical terminals 70 and 71 extending from respective ends thereof. The electrical resistor 68 is supported coaxially within the jacket 60 by forward and aft headblocks 73 and 75 respectively. Preferably the headblocks 73 and 75 are formed of an electrically nonconductive plastic material that enables the electrical resistor to be slid into the cylindrical body 61 through the rear end 64 during the manufacturing process. The electrical resistor 68 is encapsulated within the interior of the cylindrical body 61 by encapsulating material 78 that is electrically nonconductive but that is a relatively good heat conductor so as to transfer heat from the electrical resistors 68 to the jacket 60. Preferably the material 78 is a plastic epoxy material.

The suppository appliance 46 preferably includes a temperature sensing transducer 80 mounted within the jacket 60 for sensing the temperature of the suppository appliance 46. The transducer 80 may be from a variety of elements, such as a thermistor or thermocouple.

Electrical leads 82 extend from the transducer 80 and the resistor 68 rearward to the rear end 64. Electrical leads are individually identified as leads 82a, b, and c. During the manufacturing process the rear end 64 is sealed with a sealing material 84 such as silicone rubber which is electrically nonconductive and a rather poor heat transfer material to prevent moisture or other foreign material from penetrating to the appliance 46 and to prevent the dissipation of heat from the suppository appliance.

The cable means 52 includes a flexible electrical cord 86 that extends from the rear end 64 of the suppository appliance 46 a sufficient distance for connecting to an appropriate electrical receptacle on the control case. The cord 86 has three electrical conductors therein for connecting to the electrical leads 82a–c. The opposite end of the electrical cord 86 has an electrical connector and more specifically a male plug or jack 89 fixed thereon for releasably mating with a corresponding electrical connector or receptacle on the control case 48. The male plug 89 includes at least three spaced prongs 90 projecting therefrom for electrically connecting to a case connector.

The portable control case 48 includes a housing 92 that is sufficiently lightweight to be easily hand carried by the patient or strapped to a belt or sling. The housing 92 includes a battery compartment 94 for receiving the electrical battery 50. Additionally the housing 92 includes an electrical connection such as an electrical socket or common receptacle 96 (FIG. 5) that has female cavities for receiving the prongs 90.

The housing 92 further includes an exposed temperature control knob 98 that is movable to enable the patient to turn the device on and off and to adjust the temperature of the suppository appliance 46.

The electrical storage batteries 50 are preferably mounted in a battery pack 100 that is insertable and removable from battery compartment 94. Preferably the batteries 50 are of the rechargeable type and may be used over and over again. The batteries 50 preferably have a maximum voltage rating of less than 12 volts.

The control means 54 more specifically illustrated in FIGS. 6 and 7 includes a power supply network 102 that is connectable to the electrical storage battery 50. The network 102 includes an on-off switch 104 that is activated by turning the knob 98 to enable the patient to initiate and terminate the therapeutic treatment when desired. The power supply network 102 further includes power supply lines 106, 107.

The control means 54 includes a temperature selection network 108 that includes an adjustable resistor or potentiometer 110 which is included in a circuit between the power supply lines 106, 107 for selecting a desired temperature. Potentiometer includes a tap line 111.

The control means 54 further includes an energy control network 113 that is responsive to the output of the temperature selection network for controlling the application of electrical energy from the battery 50 to the suppository appliance resistor 68. In a preferred embodiment the energy control network 113 includes an emitter follower transistor circuit 124 that is operatively connected between the power lines 106, 107 and is responsive to the output of the signal from the temperature selection network 108, applied at the base of the transistor 124 for transmitting energy to the suppository appliance 46 along output line 126.

In the embodiment illustrated in FIG. 6, the potentiometer 110 serves as a voltage selector for selecting a voltage to be applied to the base of transistor 124 so that the current supplied to the resistor 68 is proportional to the voltage selected.

In the embodiment illustrated in FIG. 7, the energy control network 113 includes a control bridge circuit 114 having an operational input/output device 115 for controlling the amount of energy applied by the transistor 124. The transducer 80 is positioned in one leg of the control bridge circuit 114 and the variable potentiometer is positioned in another leg. The operational input/output device 115 provides an output signal on line 120 to the transistor 124 that is responsive to the magnitude of the voltage imbalance across the control bridge circuit 114.

In FIG. 7, the tap line 111 serves to subdivide the potentiometer 110 into two legs on one side of the bridge circuit 114 with the appliance transducer 80 and a fixed resistor on the other side of the bridge circuit 114. In an alternate configuration, illustrated in FIG. 8, the bridge circuit 114 has two fixed resistors on one side and the appliance transducer 80 and the variable potentiometer 110 on the other side. The advantage of the configuration illustrated in FIG. 8 is that the voltage sensed by the device 115 from one side of the bridge circuit is constant from the two fixed resistors and is independent of the voltage setting of the adjustable potentiometer 110 or the voltage across the variable transducer 80.

The operational input/output device 115 preferably includes a voltage comparator or operational amplifier 116 (FIGS. 9 and 10) that receives input signals from both sides of the bridge circuit 114. The comparator 116 (FIG. 9) compares the voltage from the input lines 117 and 118. If the temperature sensed by the transducer 80 is less than the temperature selected by the patient, then the imbalanced voltage across the bridge circuit 114 is applied to the voltage comparator 116 to drive the transistor 124 to increase the flow of electrical energy to the suppository appliance 46. If the temperature sensed by the transducer 80 is greater than the temperature set by the patient then the transmission of electrical energy from the battery 50 to the suppository appliance is discontinued or reduced.

In an alternate embodiment illustrated in FIG. 10 the control bridge circuit 114 includes a continuous proportional control subcircuit 135 for controlling fluctuations in the temperature of the suppository appliance 46 with respect to the temperature set by the patient. The continuous proportional control subcircuit 135 is designed to limit the degree of "overshooting" or "undershooting" of the temperature. This is frequently referred to as dampening the "hunting" of the energy control network 113. The continuous proportional control subcircuit 135 includes proportional input resistors 138 and 139 mounted in input lines 117 and 118 respectively.

Subcircuit 135 further includes negative feedback loops 140 and 141 operatively connected between the operational device 116 negative input port and output line 120, and the operational device 116 positive input port and the common or ground, respectively. Feedback resistors 143 and 144 are mounted in loops 140 and 141 respectively.

The subcircuit 135 is designed so that the ratio of the resistance values of resistor 138 to resistor 143 is equal to the ratio of the resistance values of resistor 139 and resistor 144. The ratio is selected depending upon the gain desired. Preferably the resistance value of resistors 138 and 138 are equal and the resistance values of resistors 143 and 144 are equal. However, the resistor value of resistor 138 is different from the resistance value of 143. Consequently the output signal from the operational input/output device 115 to the transistor 124 on line 120 is proportional to the difference between the two input signals on lines 117 and 118 multiplied by the selected resistor ratio. Capacitors 145 and 146 are mounted in the loops 140 and 141 respectively, parallel with resistors 143 and 144 to provide static and dynamic voltage control and phase balance to the operational input/output device 115.

Preferably the proctologic device 10 includes a battery recharging unit 150 (FIG. 2) that has a plug-in voltage reduction module 151 with an electrical cord 152 extending to a plug or jack 153 that is compatible with the common receptacle 96. However, the jack 153 is designed so that the recharging lines interconnect with different receptacle elements in the common receptacle 98 than the prongs 90. The device 10 is designed so that the recharging unit 150 cannot be connected to the receptacle 98 of the case 48 while the suppository appliance 46 is connected. In this manner the possibility of electical shock from a high voltage source is eliminated.

During the operation of the proctologic device 10, the suppository appliance 46 is placed in the anal canal with the appliance 46 extending through the anal canal with the distal tip 63 communicating with the rectum 14 so that the entire anal canal 16 is in intimate contact with the heat transfer surface 66 of the suppository appliance and so that the suppository appliance 46 is in good contact with the internal hemorrhoid 42 and the external hemorrhoid 44.

The suppository appliance 46 is then internally heated utilizing the electrical resistor 68 to a temperature above the patient's body temperature. The temperature of the suppository appliance 46 is then controlled by the control means 54 so that the temperature does not exceed 45° C. to sufficiently heat the anal canal without injuring body tissues to thereby relax the sphincter muscles 20 and to hopefully dilate the blood vessels of the hemorrhoids 42, 44 to promote increased blood flow therethrough. The temperature in the suppository appliance 46 is sensed by the transducer 80 with an automatic control existing to make sure that the temperature of the appliance 46 is maintained between the patient's body temperature and 45° C.

The suppository appliance 45 is provided with sufficient surface area to make sure that between 5 square centimeters and 20 square centimeters of the suppository appliance are in intimate contact with the anal canal 16 to provide sufficient therapeutic treatment. Furthermore, the electrical circuits are designed so that heat transfer surface 66 transfers heat from the suppository to the surrounding tissues at a heat flux of between 0.01 watts per square centimeter and 0.10 watts per square centimeter.

It should be understood that the above-described embodiments are simply illustrative of the principles of this invention and that numerous other embodiments may be readily devised by those skilled in the art without deviating therefrom. Therefore only the following claims are intended to define this invention.

What is claimed is:

1. A proctologic device for the therapeutic treatment of external and/or internal hemorrhoids projecting from the wall of a patient's anal canal which extends from the anus to the rectum and is surrounded by sphincter muscles; comprising:
   an anal canal appliance for insertion into the anal canal through the anus;
   said appliance having an elongated cylindrical body with an external heat transfer surface extending from a front end to a rear end for intimately contacting the anal canal wall and the projecting hemorrhoids;
   said external heat transfer surface having a diameter sufficient to expand the anal canal and effectively transfer heat from the heat transfer surface to the anal canal wall and the hemorrhoids without painfully stretching the sphincter muscles;
   said appliance having an electrical resistor heating element mounted internally within the cylindrical body for converting electrical energy to thermal energy;
   said appliance having an efficient solid heat transfer medium within the body encapsulating the electrical resistor heating element for transferring thermal energy from the electrical resistor heating element to the external heat transfer surface;
   a source of electrical energy;
   a cable means extending between the source and the appliance for operatively connecting the source to the electrical resistor heating element;
   a temperature transducer in the body for sensing the temperature of the external heat transfer surface and for producing an electrical temperature signal corresponding to the temperature of the external heat transfer surface;
   control means operatively connected to the electrical energy source and responsive to the electrical temperature signal for automatically regulating the amount of electrical energy applied to the electrical resistor heating element to heat the external heat transfer surface and to maintain the external heat transfer surface at a preset temperature between body temperature and 45° C. to thereby relax the sphincter muscles and to facilitate the opening of vascular channels of the hemorrhoids to facilitate shrinkage of the hemorrhoids.

2. The proctologic device as defined in claim 1 wherein the external heat transfer surface has a length between 30 millimeters and 50 millimeters.

3. The proctologic device as defined in claim 1 wherein the external heat transfer surface has an area between five square centimeters and twenty square centimeters.

4. The proctologic device as defined in claim 1 further comprising a portable case capable of being easily carried by the patient and wherein the source of electrical energy includes an electrical storage battery mounted in the case.

5. The proctologic device as defined in claim 4 comprising a recharging network operatively connected to the electrical storage battery and wherein the cable means includes an appliance jack wherein the case has an exposed common electrical connector fixture that is operatively connected to both the recharing network and the control means for receiving either a recharging jack or the appliance jack but not both at any one time.

6. The proctologic device as defined in claim 1 wherein the control means includes an energy control network means for comparing the temperature sensed by the temperature transducer with the preset temperature and for adjusting the rate at which electrical energy is applied to the electrical resistor to maintain the external heat transfer surface at the preset temperature between body temperature and 45° C.

7. The proctologic device as defined in claim 6 wherein the energy control network means includes a balanced control bridge circuit having a variable resistor in one leg thereof that may be adjusted to a resistance value corresponding to the preset temperature and wherein the balanced control bridge circuit has the temperature transducer electrically connected in another leg thereof.

8. A protologic process for the therapeutic treatment of external and/or internal hemorrhoids projecting from the wall of a patient's anal canal, in which the anal canal extends from the anus to the rectum and is surrounded by the sphincter muscles, comprising:
   placing an anal canal appliance in the anal canal in which the appliance has an external heat transfer jacket with a diameter sufficient to expand the anal canal to intimately contact the anal canal wall and a length sufficient to extend from the anus to the rectum;
   internally heating the jacket to a temperature in the anal canal so that the temperature of the jacket does not exceed 45° C. to heat the anal canal without injuring anal canal tissues to thereby relax the sphincter muscles and to dilate blood vessels of the hemorrhoids to promote blood flow therein;
   sensing the temperature of the jacket in the anal canal; and
   automatically controlling the application of heat to the jacket in response to the sensed temperature of the jacket to maintain the temperature of the jacket at a preset temperature above the patient's body temperature and below 45° C.

9. The proctologic process as defined in claim 8 wherein the process includes heating the jacket sufficiently so that the heat flux from the jacket to the surrounding anal canal has a heat flux of between 0.01 watts per square centimeter and 0.10 watts per square centimeter.

* * * * *